(12) United States Patent
Friberg

(10) Patent No.: US 8,308,627 B2
(45) Date of Patent: Nov. 13, 2012

(54) MEDICAL AND RECREATIONAL MAGNETIC DEVICE AND METHOD OF USING IT

(76) Inventor: Walter Friberg, Buffalo Grove, IL (US)

( * ) Notice: Subject to any disclaimer, the term of this patent is extended or adjusted under 35 U.S.C. 154(b) by 615 days.

(21) Appl. No.: 12/584,185

(22) Filed: Sep. 1, 2009

(65) Prior Publication Data

US 2010/0056846 A1  Mar. 4, 2010

Related U.S. Application Data

(60) Provisional application No. 61/190,590, filed on Sep. 2, 2008.

(51) Int. Cl.
*A61N 00/00* (2006.01)
(52) U.S. Cl. .............................................. 600/9; 600/13
(58) Field of Classification Search ................ 600/9, 13, 600/14, 15; 128/897, 898, 899
See application file for complete search history.

(56) References Cited

U.S. PATENT DOCUMENTS

| | | | |
|---|---|---|---|
| 5,014,981 A | 5/1991 | Prelich | |
| 5,370,430 A | 12/1994 | Mozafari | |
| 6,139,486 A * | 10/2000 | Matuszewski et al. | 600/15 |
| 6,267,782 B1 * | 7/2001 | Ogle et al. | 623/1.1 |
| 6,287,484 B1 | 9/2001 | Hausslein et al. | |
| 6,322,491 B1 | 11/2001 | Bove et al. | |
| 6,779,199 B1 | 8/2004 | O'Dea et al. | |
| 7,373,740 B2 | 5/2008 | Lo | |
| 2002/0151759 A1 * | 10/2002 | Paturu | 600/15 |
| 2005/0215842 A1 * | 9/2005 | Pilla et al. | 600/9 |

* cited by examiner

*Primary Examiner* — John Lacyk
*Assistant Examiner* — Joshua D Lannu

(57) ABSTRACT

A medical and recreational device comprises at least two laminas. The laminas comprise sources of magnetic field. The sources of the magnetic field located on one of the laminas faced to another one completely or partially by like and/or unlike magnetic poles and at least one of said laminas configured to be attached to the treated body part.

11 Claims, 13 Drawing Sheets

ASTRONAUT'S BOOT

MEDICAL AND RECREATIONAL MAGNETIC DEVICE AND METHOD OF USING IT

This application claims priority from U.S. Provisional Application 61/190,590 filed Sep. 2, 2008, the entire disclosure of which is incorporated herein by reference

BACKGROUND OF INVENTION

The present invention relates to improvement of medical and recreational devices designed for shock absorbing and energy return during ambulation and exercise, unloading of the various parts of body, affected by trauma or injury, prevention and treatment of contractures and at the same time provides with the synergetic health benefits of magnetic field, as well as minimizing negative consequences of weightless environment, and the Earth magnetic field deprivation during the space expeditions.

The invention related to the medical use of the magnetic field created by ether constant magnets or electromagnets.

There are multiple variants of using the magnetic field for shock abortion ? for instance, during car collision (see for example U.S. Pat. No. 5,370,430 incorporated in this application by reference) and exercising devices (see for example U.S. Pat. No. 5,014,981 incorporated in this application by reference). There are magnetic gloves designed for handling of small metal components (U.S. Pat. No. 6,779,199 incorporated in this application by reference). The patents as well as other known devices used the concept do not designed for the above-mentioned purposes of the invention.

The concept of health benefits of magnetic fields is widely accepted. There are multiple variants of medical device using this concept. See for example, flexible magnetic insole (U.S. Pat. No. 6,322,491 incorporated in this application by reference).

There are also multiple devices designed to counteract wrist and fingers flexion or extension contraction such as wrist-extensor finger-flexion orthosis, pancake splint, wrist extensor hinge/spring assist-long opponents orthosis, knuckle bender orthosis, dorsal MCP extensor stop orthosis, C-bar opponents orthosis. All the above devices are bulky, inconvenient to use, heavy, do not have healing properties of magnetic field, do not antibacterial properties, and do not provide a good access to the patient skin and wound for hygiene and other medical care.

Major disadvantages of all of these devices are absence of the shock absorbing and energy return properties, absence of possibility to use them as an exercise tool during every activities, as well as absence of possibility to easily redesign the device depends on the individual's needs, for example in case leg length discrepancy, foot drop, heel pain est.

It is known the shaped memory insole structure with re-adjustable supporting pads (U.S. Pat. No. 7,373,740 incorporated in this application by reference). This type of insoles provides some shock absorbing during loading response and midstance of stages of the gait cycle. However, it doesn't provide benefits of magnetic field and exercise as well. Another disadvantage of the insole is absence of return energy after the pressure on the insole released during unloading stages of the gait.

OBJECTS OF THE INVENTION

There are objects of the present invention to provide shock absorbing, energy return and possibility of exercise, possibility of easily redesign of the device depends of the client's needs and during his/her everyday activity, promote the damaged tissue repair by providing "antigravity position" of the damaged extremity in conjunction with healing benefits of magnetic field.

The present invention comprising two or more laminas contented sources of the magnetic field, said sources of the magnetic field located on one of the laminas faced to another one completely or partially by the like and/or unlike magnetic poles, and at least one of said laminas is congruent to the treated part of body and attached to the body part. The magnetic field used in said medical and recreational device created by ether constant magnets or electromagnets. Said medical and recreational device can be attached to different body parts for example feet, hands, and extremities.

The variant of the present invention embodiment for lower extremity used as an insole designed to ease foot fatigue especially during prolonging standing and walking, absorb shock during running, preservation of normal foot anatomy, relieve foot pain and swelling connected with arthritis, neuropathy, neuromas, heel spurs, and plantar fasciitis and foot muscle sprain and strain, rehabilitation after trauma and foot surgery. During the Space expedition the proposed device helps to preserve a normal foot anatomy, especially arches, as well as minimize side effects of weightless on the foot bones, ligaments, and muscles. The device mimics normal Earth magnetic field during the Exploration missions. Magnetic field generated by the device magnets possible can act on proprioceptors on soles and also minimize negative effects of the weightless conditions.

Special versions of the present invention as insole can be used as an exercise device in the weightless conditions. Measurements of forces during exercise in a space suggested that much less force was experienced than would be experienced when exercising on Earth. One of the important benefits for astronauts of the embodiment is the possibility to generate the muscle efforts against the magnetic field. These efforts do not depend on the space weightless conditions and solely connected with intensity of the magnetic field. In addition, the basic concept of the proposed invention can be used for the training exercise of practically any skeletal muscles during the Exploration missions, as well as in an everyday activity.

Other versions of the proposed device can be used for upper and lower extremities as well as virtually for any body part counteract with contractures, promote healing processes, providing "antigravity position" of the damaged extremity in conjunction with healing benefits of magnetic field.

The variant of the proposed embodiment for upper extremity designed to counteract wrist and fingers, wrist, elbow and shoulder contraction, for relief hand pain, control edema and decrease hand fatigue, as well as treatment hand arthritis, carpal tunnel syndrome and other nerve conditions affected hand, rehabilitation after trauma and hand surgery, as well as hand and upper extremity exercise.

The present invention employs the concept about the repulsion of like magnetic poles and attraction of unlike ones for the prevention and treatment of fingers and toes flexion and extension contractures, foot drop, wrist flexion and extension contractures, leg discrepancy, providing a good access to the patient's skin for hygiene and therapeutic intervention, prevention and treating wound infection, pain relief and edema control, hands and feet exercises, and improving of upper and lower extremities activities of daily living for patients with arthritis, after stroke, spinal cord injury, burn injury, and peripheral nerve injuries, minimizing consequences of trauma and injury by unloading the affected body part, as well as minimizing negative consequences of weightless environment, and the Earth magnetic field deprivation during the space expeditions.

DESCRIPTION OF THE PREFERRED EMBODIMENTS USING FOR FEET (INSOLE) AS AN EXAMPLE

Figure 1:
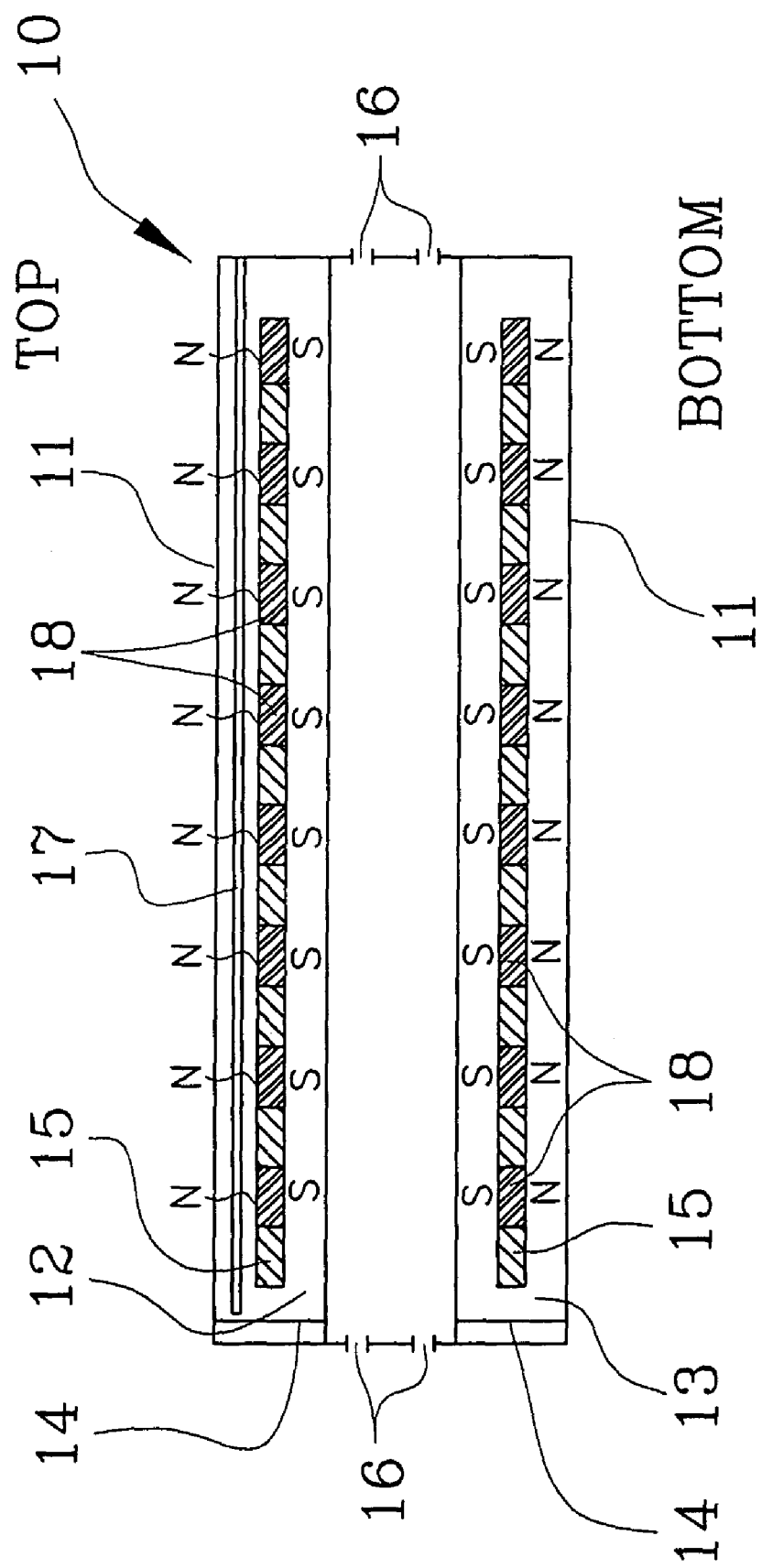
FIG. 1 represents the common variant of the embodiment for feet—insole

The insole 10 (FIG. 1) comprising cover 11 having inside two rows of horizontal pockets: top pocket 12 and bottom pocket 13, side accesses 14 to pockets 12 and 13.

In each pocket inserted flexible magnetic lamina 15. Sides of the cover 11 between the top and bottom pockets have perforations 16. Above the top magnetic lamina 15 can be inserted a magnetic shield 17.

Figure 2A:
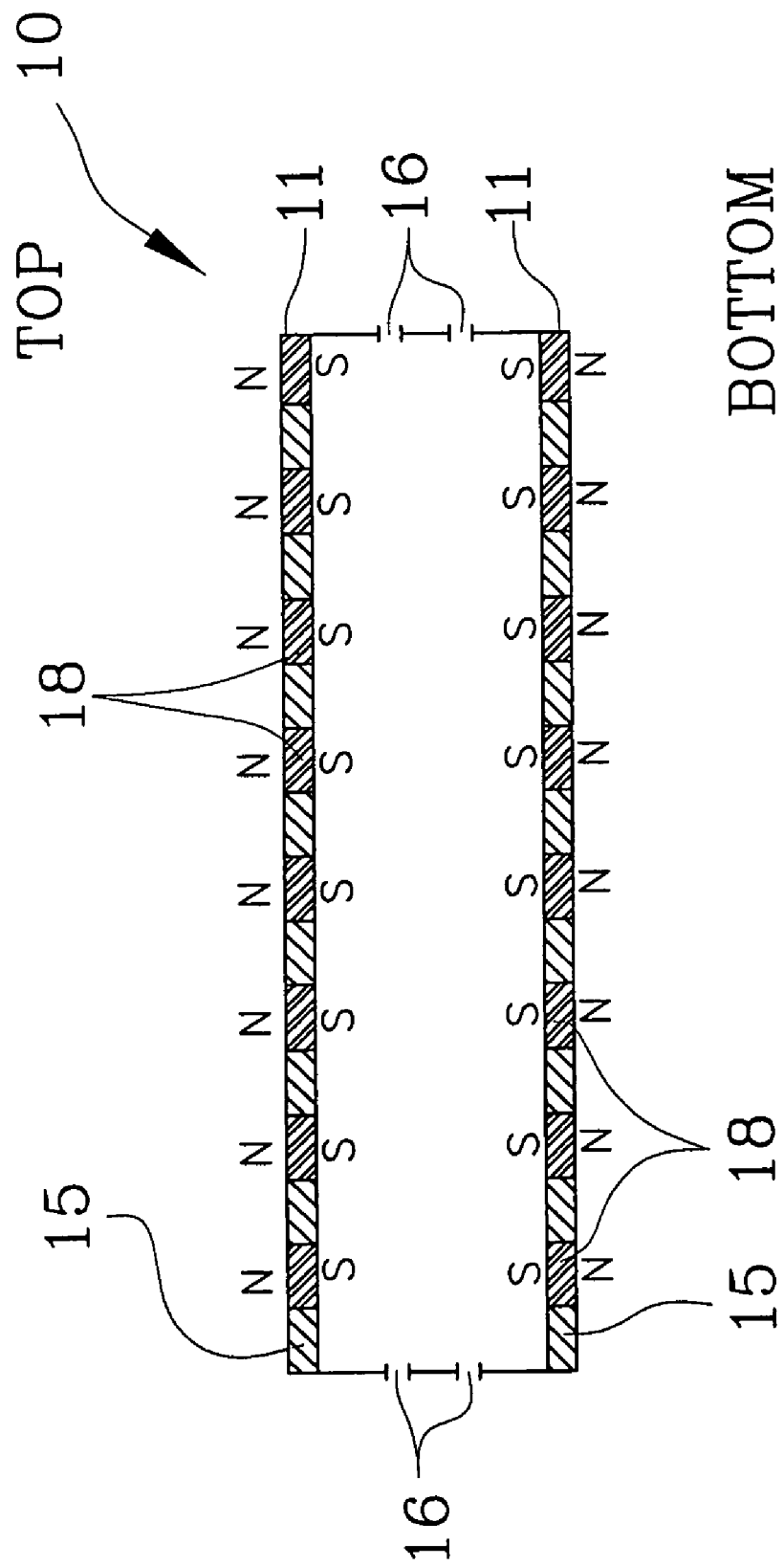
FIG. 2A represents a side view of the simplest variant of the embodiment for feet

The top and bottom laminas 15 have embedded magnets 18. The top lamina has magnets 18 facing like pole to the magnets 18 of the bottom lamina: South-to-South or North-to-North The insole 10 (FIGS. 2A and B) included two magnetic laminas 15 with embedded magnets 18. The sides of the laminas 15 attached to the cover 11. Sides of the cover 11 between the top and bottom magnetic laminas 15 have perforations 16.

Figure 3:
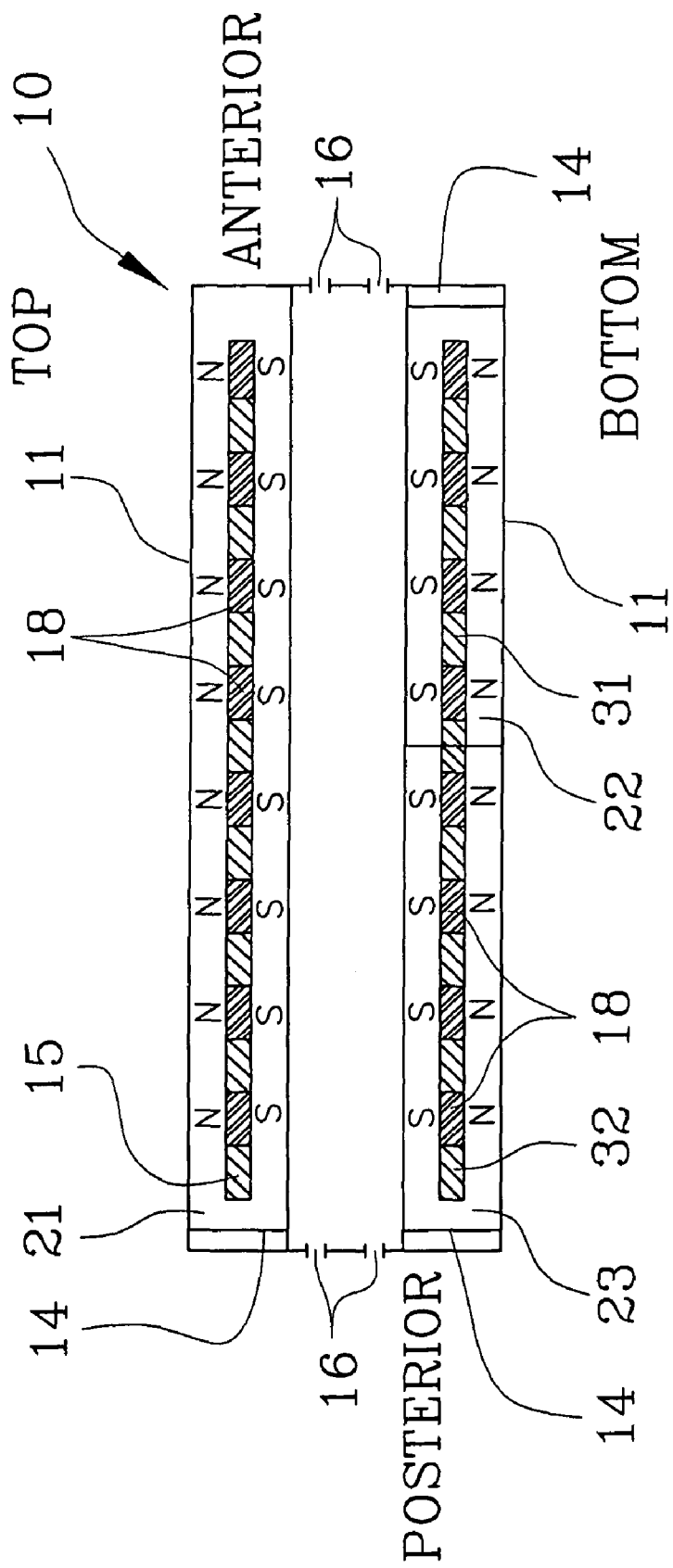
FIG. 3 represents the variant of the embodiment for feet

The variant of the proposed embodiment presented on FIG. 3 shows the insole 10 with one top pocket 21 and two bottom pockets: anterior pocket 22 and posterior pocket 23. In the top pocket 21 inserted magnetic lamina 15 the anterior pocket 22-inserted magnetic lamina 31 and in the posterior pocket 23-inserted magnetic lamina 32.

A mirror position of pockets: two top pockets and one bottom pocket is also possible.

Figure 4:
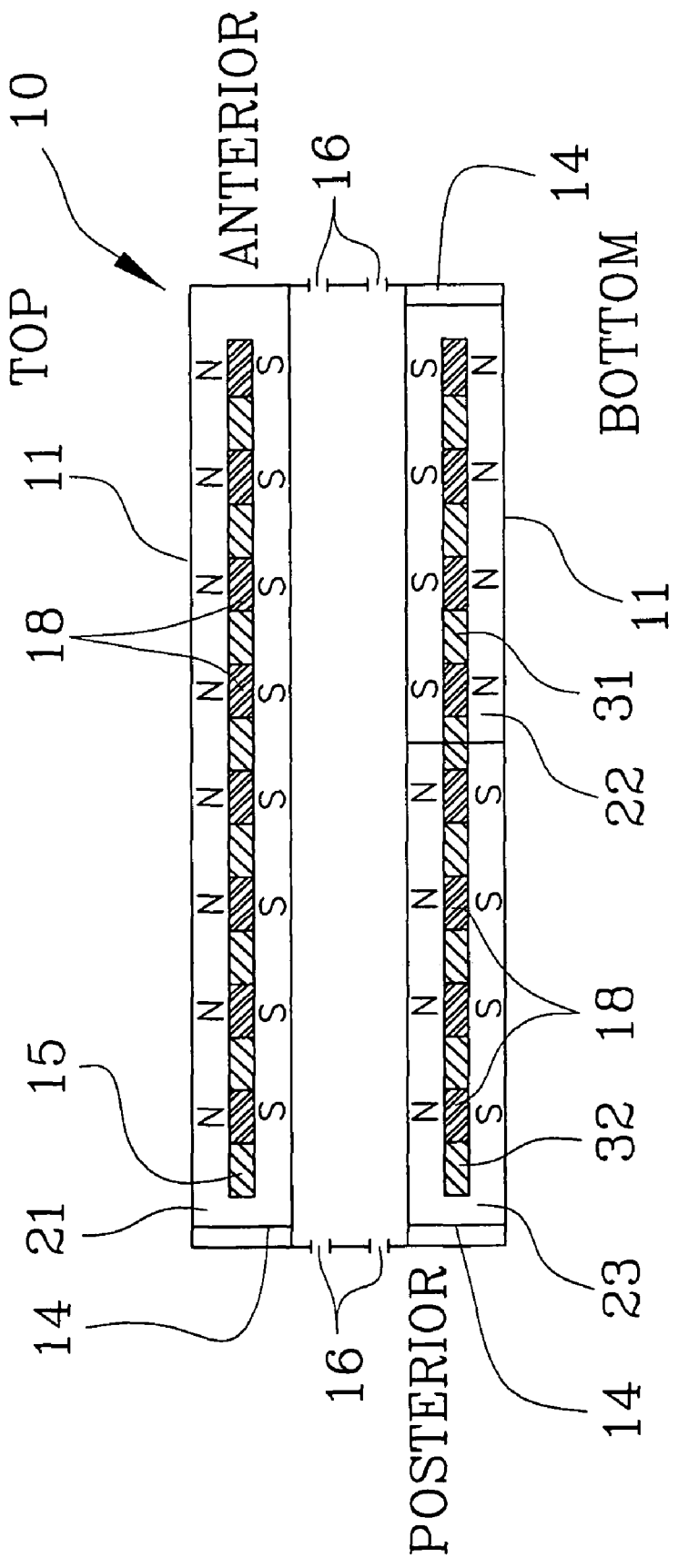
FIG. 4 represents a variant of orientation of three magnetic laminas using the variant for feet as an example
Figure 5:
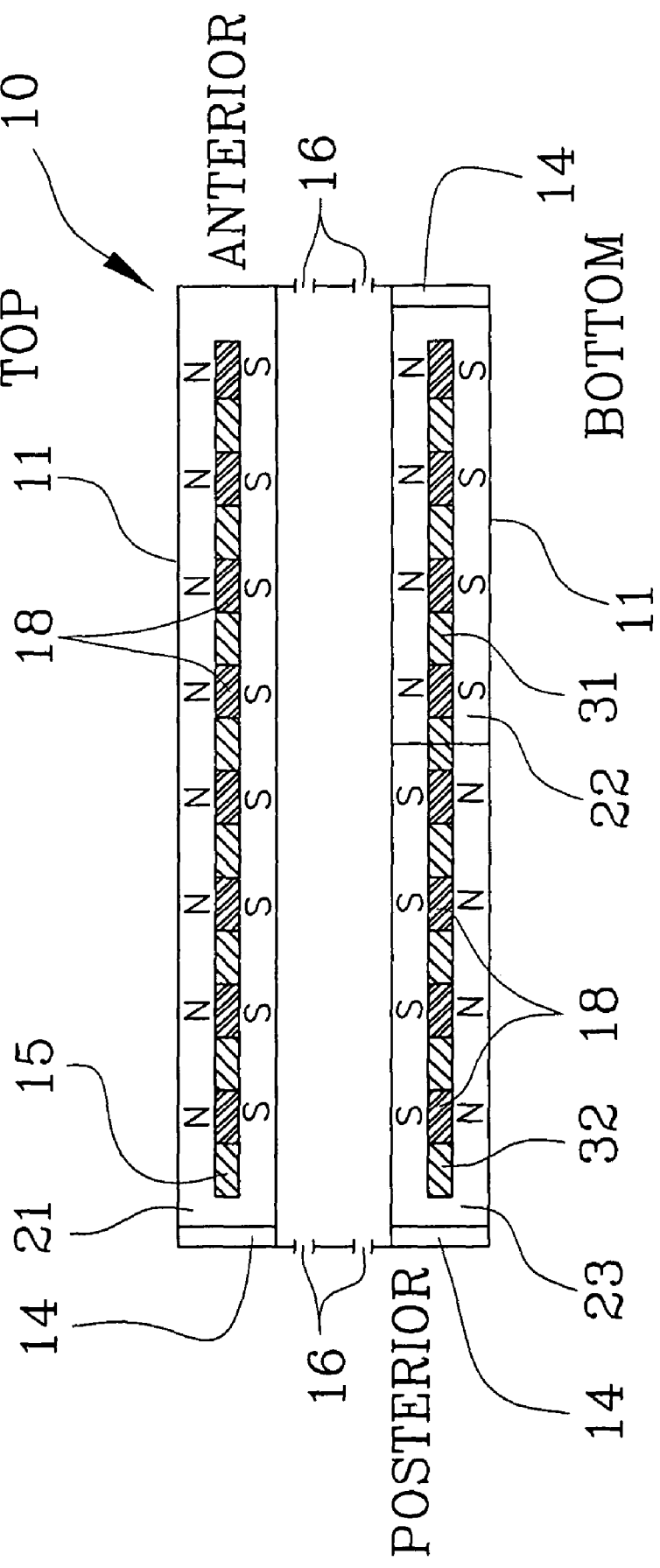
FIG. 5 represents another variant of orientation of three magnetic laminas using the variant for feet as an example

FIG. 4 shows variants of orientation of polarity of three magnetic laminas: 15, 31, and 32 for foot drop FIG. 5 shows variants of orientation of polarity of three magnetic laminas 15, 31 and 32 for heel pain and "heel lifting".

Figure 6:
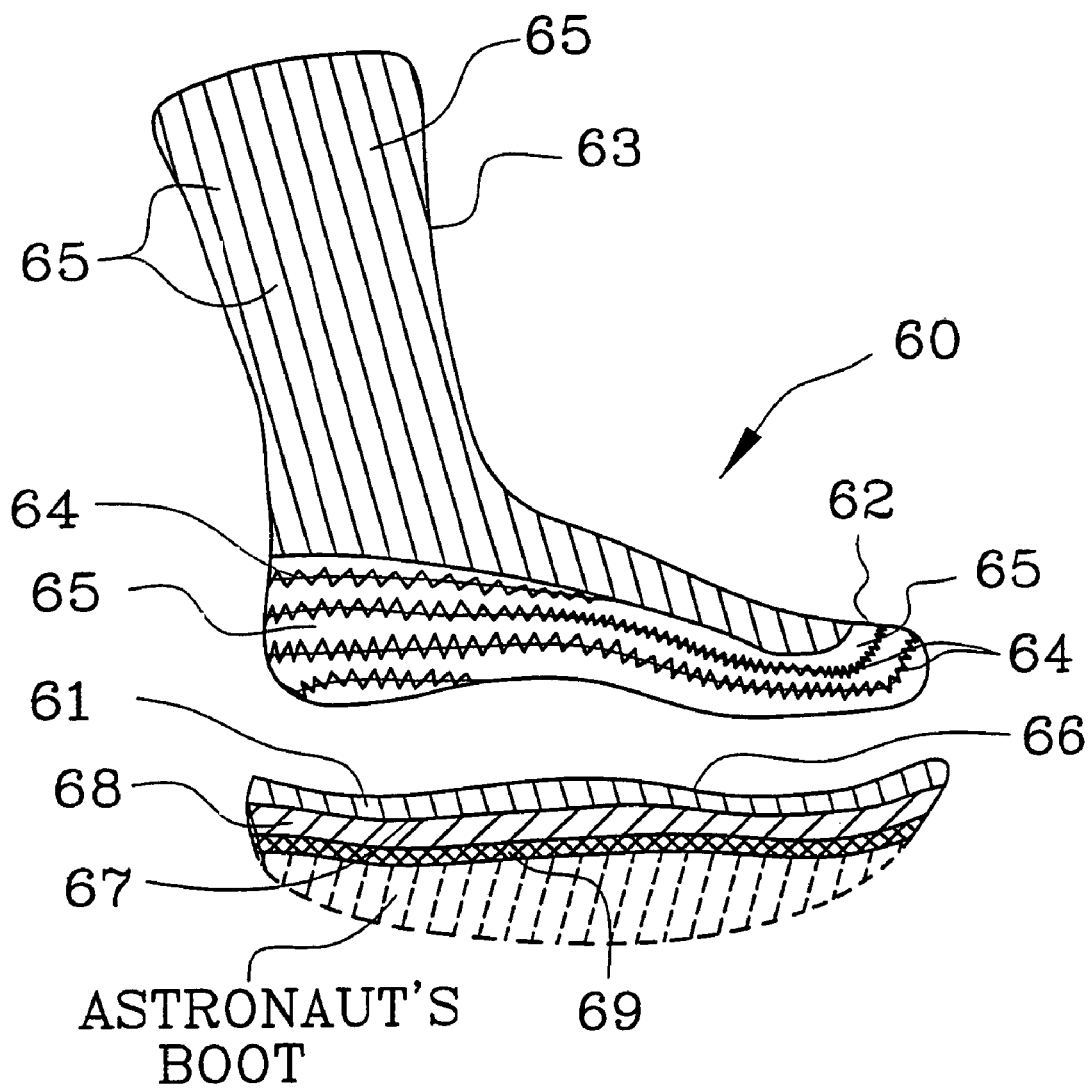
FIG. 6 represents a magnetic sock and magnetic base.

FIG. 6 shows a magnetic sock 60 and magnetic base 61.

The sock 60 has two portions: a lower (plantar) portion 62 and an upper (dorsal) portion 63.

The lower portion 62 has a mesh "galosh-like" shape follows the contour of the arches.

The lower portion 62 is a mesh "galosh" made from magnetic laminas 64 (preferably thin and narrow ones) embedded in nonmagnetic materials. Upper portion 63 made from nonmagnetic fibers 65.

The upper side 66 of the magnetic base 61 faced to lower portion 62 of the magnetic sock 60 and contralateral side 67 of the magnetic base 61 attached to the magnetic shield layer 68. The magnetic shield 68 has an adhesive layer 69 for attaching to the inner side of the astronaut's boot. A round outer contour of the boots is preferably.

Figure 7:
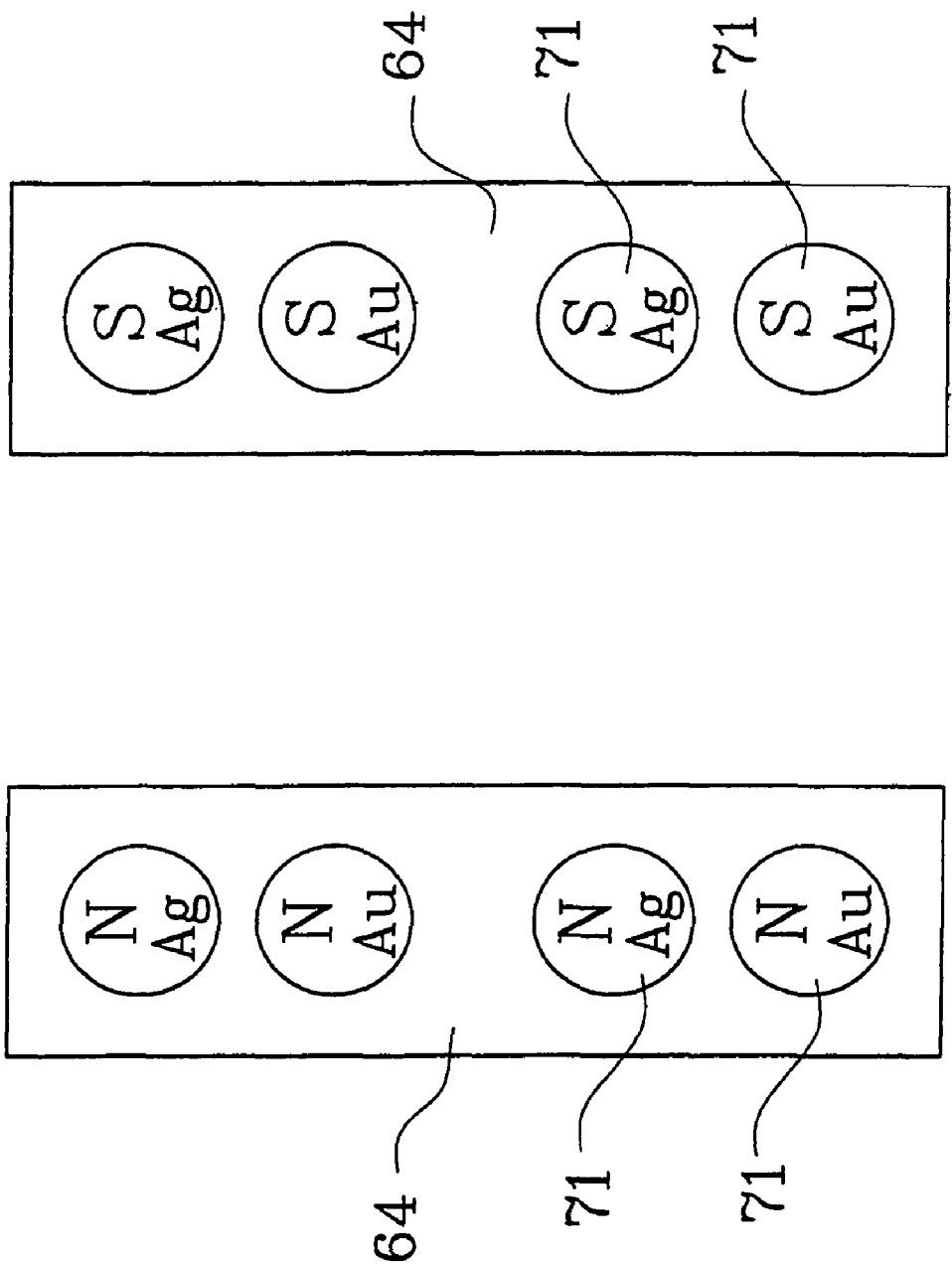
FIG. 7 represents positions, polarity, and materials of metallic coating of magnets in the magnetic lamina.

FIG. 7 shows the magnetic lamina 64. The magnetic lamina 64 consistent from the thin, narrow polymeric band with embedded magnets 71. The magnets have either silver or gold coating. Other metals can be used for coating, for example copper and platinum. However, at list two different metals must be used.

Figure 8A:
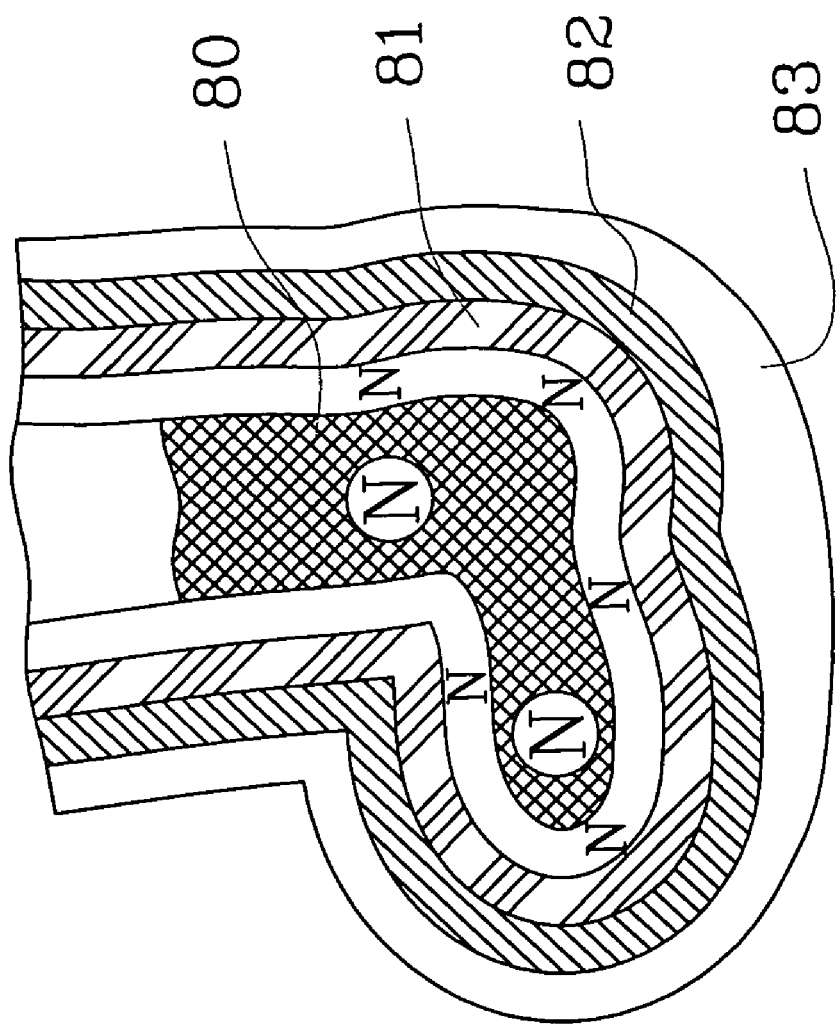
FIGS. 8A and B represents magnetic half-hose within an astronaut's boot
Figure 9:
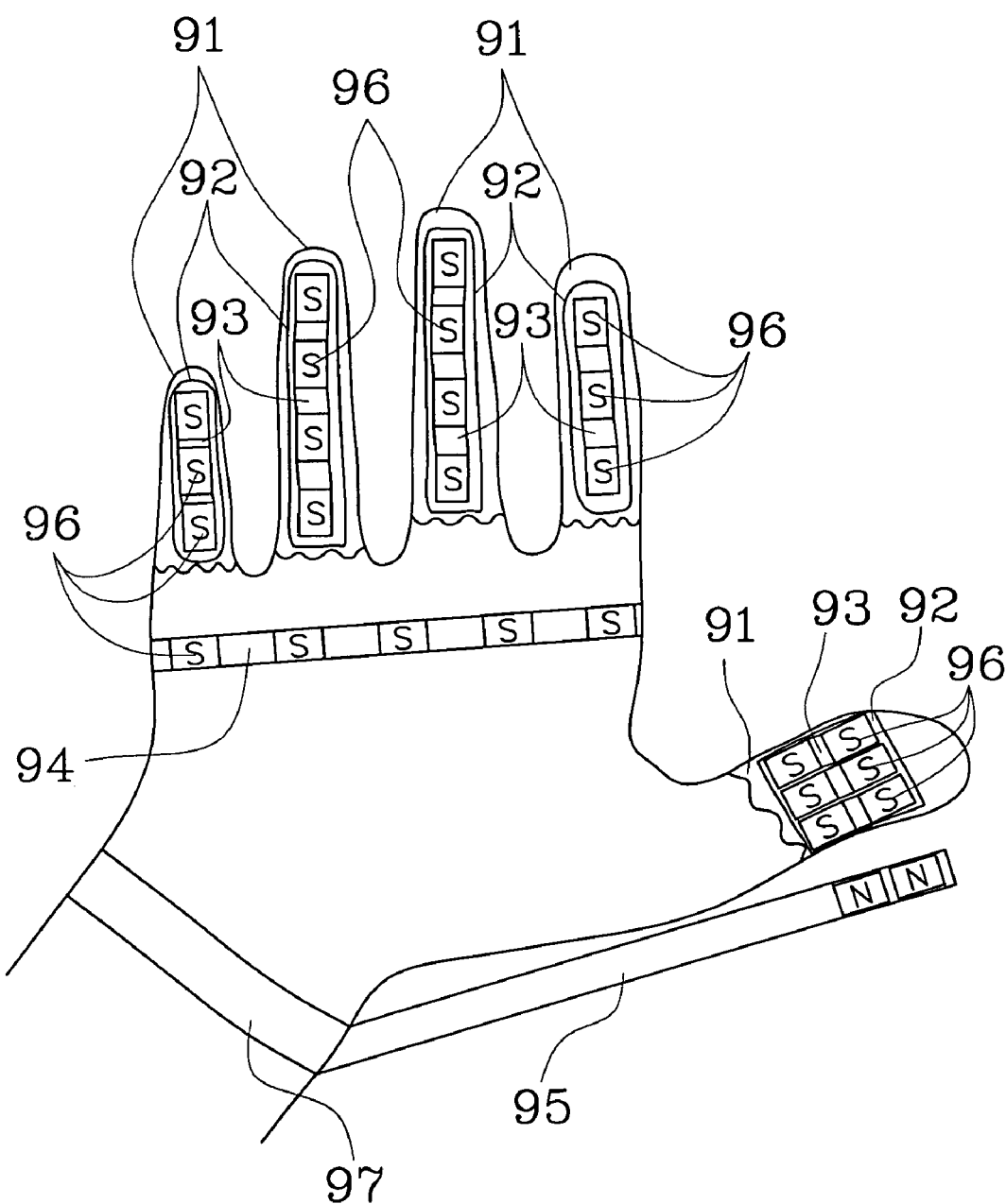
FIG. 9 represents a variant of the proposed devised for hands.

FIGS. 8A and B show the magnetic half hose 80. The half hose 80 surrounded by magnetic lamina 81 armed by magnetic shield 82 and attached to the inner side of the astronaut's boot 83. FIGS. 8A and B show variants of orientation of polarity of the outer side of magnetic half hose 80 and magnetic lamina 81 FIG. 9 shows magnetic finger caps 91, the caps contents pockets 92 with inserted laminas 93. Bars 94 and 95 contents from laminas 93 with embedded magnets 96. The bar 95 attached to the wrist by the wrist strap 97

Figure 10:
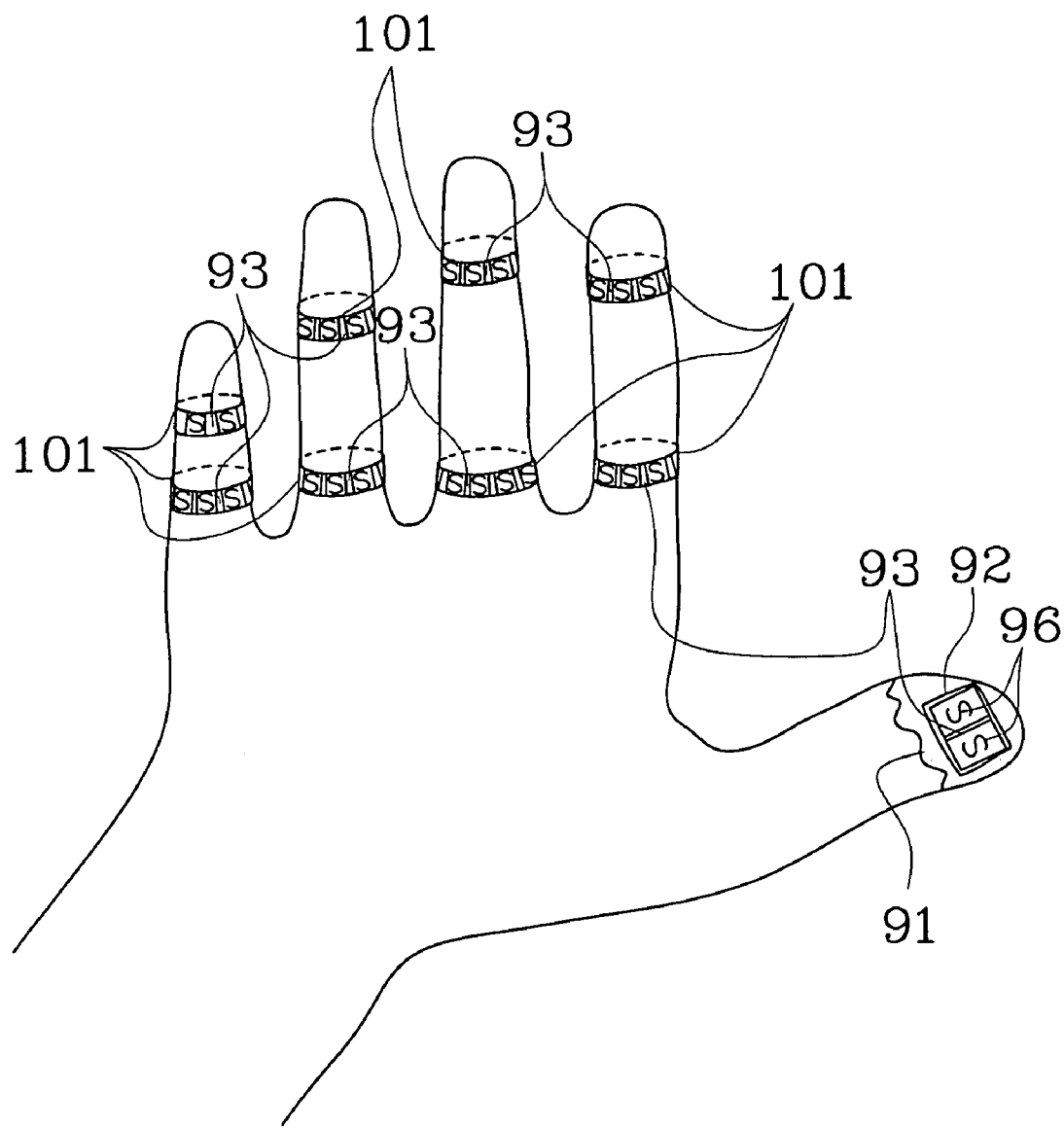
FIG. 10 represents a variant of the proposed embodiment of the hand exercise

FIG. 10 showed a finger cap 91 inserted on a thumb the cap contents pockets 92 with inserted lamina 93 with embedded magnets 96. Magnetic rings 101 made from laminas 93 with embedded magnets 96.

Figure 11:
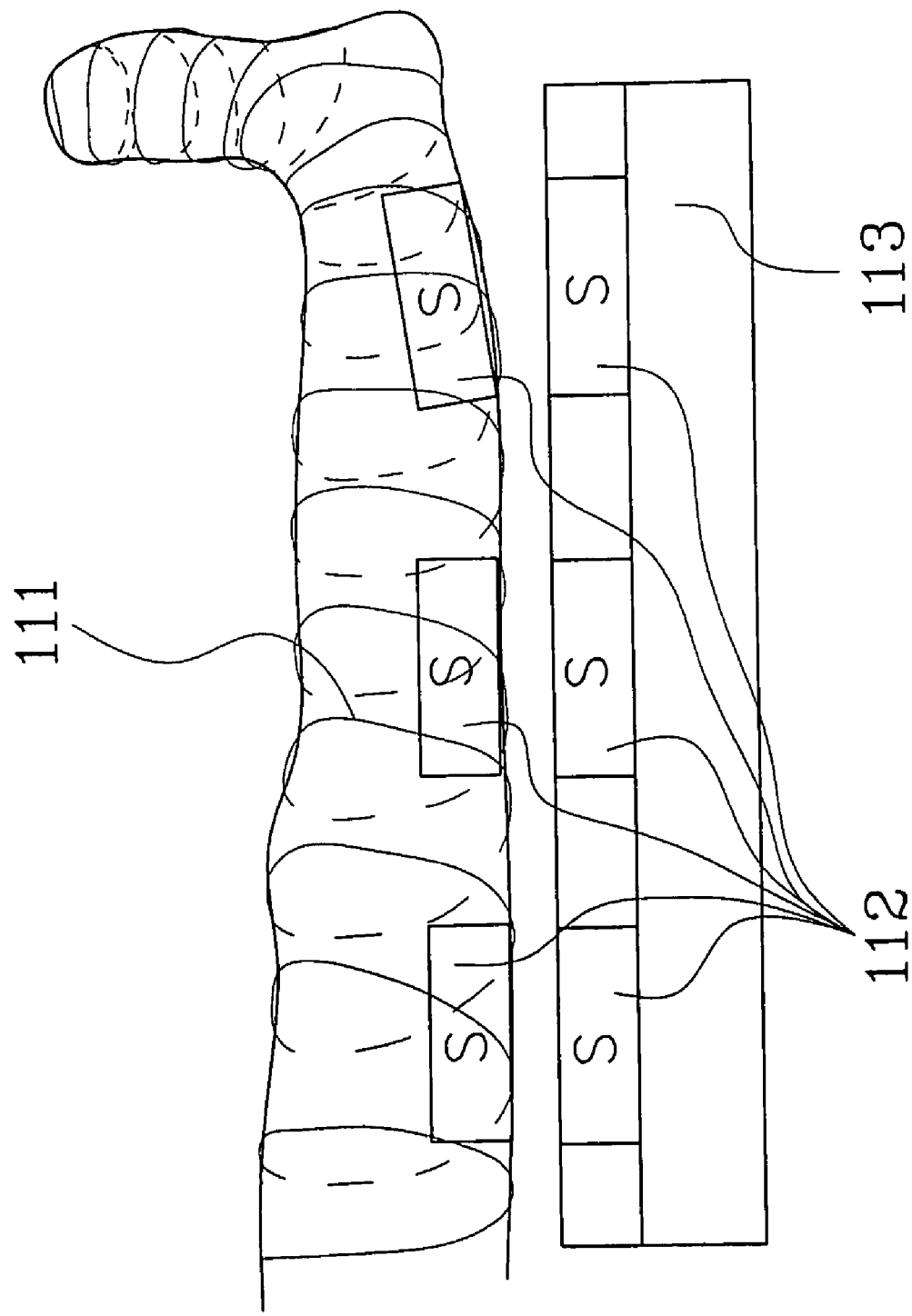
FIG. 11 represents a variant of the extended magnetic gloves and a magnetic lamina for the "antigravity treatment" of the damaged extremity

FIG. 11 showed damaged dressed extremity 111 magnets 112 attached to the dressing and the bed surface 113.

The detailed description set forth below in connection with the appended drawings is intended as a description of presently preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequence may be accomplished by different embodiments that are also intended to be encompassed within the spirit and scope of the invention.

The basic concept of the embodiment is a dual use source of magnetic field.

On one hand the sources of magnetic field grants the devise the benefits of magnetotherapy, and on the another hand the sources of magnetic field acts as a shock absorbing and energy return mechanism without any additional tool. The device has several advantages over conventional orthosis For example thermoplastic molded ankle foot orthosis (AFO) made from special semi-rigid materials is bulky and required custom making. The Double Metal Upright AFO contents multiple springs and pins and also bulky and inconvenient. It should be stressed that the shock absorbing is not significantly decreased due to wear and tear like in the coil—arm insoles and energy return mostly depends on intensity of the magnetic field and pressure affords and is not wasted for the changing of configuration of the spring or semi-rigid materials itself.

In this embodiment the constant magnetic field provides at the same time five different heath benefits:

1. Magnetotherapy to decrease pain and edema and improve circulation

2. Intensification of iontophoretic antimicrobial effect of metals used for the magnets coating.

3. Shock absorbing and energy returning property the proposed variant of device used as insole.

4. Feedback during foot/hand/extremity exercises.

5. Unloading damaged body part

The above health benefits act in a synergetic manner.

A stretchable polymeric material used for the insole is not only encased the magnets acting as a holder for magnets, but also provides the follow health benefits:

1. It provides the insole with the possibilities of heat and cooling therapy. The heat and/or cooling therapies act synergistically with magnetotherapy for improve circulation, relief pain, inflammation, fatigue, and edema.
2. It acts as an additional shock-absorbing tool increasing a pressure absorption action of magnetic field.
3. It acts as an additional energy return system Different active parts of the embodiment act in synergetic manner.

For example, a patient with diabetic neuropathy needs to improve circulation, relieve pain and edema in lower extremities, protect feet's bones, muscles, and ligaments, improve muscles and ligaments strength, and prevent skin infection.

Application of the magnetic field improves circulation relieve pain and edema. The magnetic field generated between two like magnetic poles creates the forces to absorb shock during loading pressure on feet and return energy at the unloading stages of gait, and the same repel mechanism provides a feedback during the loading-unloading exercise. Important benefit of the proposed insole is the foot arch preservation. When the body weight is removed from the insole, due to the repel mechanism, the arches return to them original height. The stretchable polymeric materials similar to TheraBand® also have shock absorbing and energy return property. If the device prior of using placed in a refrigerator or microwave oven, the materials provide the patient with benefits of cooling or heat therapy to relief feet, hands or extremities pain and edema. Magnetic field and a metal pair used for the magnets coating provide antimicrobial effect. In the variant of the proposed device using as insole the space changing between layers of insole provides additional air exchange and improves hygienic environment around the foot, decreases bad odor and possibilities of bacterial and fungal grow.

Most of these health benefits are necessary for patients with plantar fasciitis, heel spurs, arch pain, knee and low back pain, treatment spasticity, wound care, as well as for sportsmen and general public.

Sources of magnetic field can be placed with respect of the treated body part in several ways:

1. All sources of magnetic field placed above said treated body part.
2. All sources of magnetic field placed bellow said treated body part.
3. One or more source of magnetic field placed above said treated body part and another one or more source of magnetic field placed bellow said treated body part.
4. One or more source of magnetic field surrounded said treated body part for example like sock or hose/semi-hose/gloves and another one or more source of magnetic field placed above said treated body part.
5. One or more source of magnetic field surrounded said treated body part for example like sock or hose/semi-hose/gloves and another one or more source of magnetic field placed bellow said treated body part.

Depends of therapeutic or recreational needs the sources of magnetic field faced to each other by like or unlike poles Design and Materials Used in the Proposed Embodiment Cover 11 (FIG. 1) can be made from materials commonly used for conventional covers of insoles.

However, for synergetic using cold/heating and magnetic therapy the cover material must be either safe for microwaving and/or refrigerating or magnetic laminas must be remove from the cover prior of placing in microwave or refrigerator. Polymer material of the magnetic lamina 15 (FIG. 1) has dual purposes: it acts as a cushion and at the same time may be used for heat or cooling therapy acting synergistically to magnetotherapy.

Magnetic lamina 15 made from the medical grade polymer materials with possibilities cooling or heating similar to TheraBand®. This material is widely available and using now for fabrication of Thera-Band Hand Exerciser. (See for example http://www.massagewarehouse.com incorporated in this application by reference.). The TheraBand® materials have different elastic properties that provide different shock absorbing. TheraBand® used for heat and cooling therapy as well.

Magnetic lamina 15 is easily accessible through the side accesses 14 (FIG. 1)

It makes possible to change intensity of magnetic field by changing laminas with different magnetic properties. Health professionals or in some cases clients may change intensity of magnetic field. It can within seconds increase or decrease shock absorbing and energy return properties of the proposed device. By changing polarity of magnetic laminas health professionals or in some cases clients can easily change configuration of the device or unload different body part.

Calculation of strength of magnetic field depends of the client's weight can be made by the bellow formula according to the U.S. Pat. No. 5,370,430 incorporated in this application by reference. Originally in the above patent the formula used for calculation the strength and size of the magnets were based on a theoretical force of impact of magnetic car bumpers:

$$F=1/2B^2A/2M_o$$

where
F=Force (in our case the client's weight) (Newtons)
B=Flux density of magnetic filed (Tesla) in air gap
A=Area of air gap (Meters$^2$)
$M_o$=Permeability of air $4\pi \times 10^3$ (svm)

For most clinical application the North Pole of magnetic laminas should be directed toward the body However, South Pole instead also may be used in some cases. There is anecdotic evidence that North Pole has sedative and analgetic property and South Pole has a tonification effect. A long-term history of using constant magnets in China and Europe empirically proved the sedative properties of North Pole for the mild sedation, control pain and edema.

Magnetic laminas can be made from different types of permanent magnets as well as electromagnets. Preferably use an axially magnetized magnet.

To generate intense magnetic fields the permanent magnet may be made from the rare earth neodymium combined with iron boron ferrite—NdFeB. Preferred characteristics of the magnet: a medical grade, round unipole NdFeB 15/32" in diameter, 1/16"-3/16" thick, magnetic induction—12,000-12,300 gauss mfg. The above neodymium magnets have a depth of penetration up to 5" To generate weaker magnetic fields rated may be used a medical grade, round unipole ceramic magnets, 1½" diameter, ½" thick, magnetic induction—3,000-4,000 gauss mfg. The above ceramic magnets have a depth of penetration up to 1.5".

It is possible to use other known medical grade magnets, for example it's possible to use magnetic nanoparticles.

To provide elastic properties to the magnetic lamina 15 magnets encased in a stretchable polymeric material.

In the particularly preferred embodiment, the magnetic lamina 15 made from the polymeric material similar or identical to TheraBand®

One of the above mentioned types of magnets embedded in the lamina 15. The thickness of lamina 15 equals to the thickness of the used magnets. Magnets of laminas 15 must be a metal platted. For magnets coating used two or more different metals—silver, platinum, cupper, gold. The pair silver-gold is preferably. In one of proposed variants of the embodiment named magnetic sock (FIG. 6) and magnetic half hose (FIG. 8) used the magnetic laminas 64 (FIG. 7) The magnetic laminas 64 consistent from the thin, narrow polymeric bands with embedded silver and gold, (or silver, gold, cupper, platinum) platted magnets.

The metallic coatings made from different metals provide the proposed insole with antimicrobial properties. (See the U.S. Pat. No. 6,287,484—Iontophoretic material. According to the patent a pair made from the metals "provided that uses controlled electrical current derived from dissimilar galvanic materials to drive oligodynamic metal ions into solution."

The above metallic coating has a dual function:
1. It shields the skin from a direct contact with magnetic material and prevents a skin irritation.
2. It acts as a galvanic element and provides the insole with antimicrobial prosperities as described in the above mentioned U.S. Pat. No. 6,287,484 incorporated in this application by reference.

The sweat produced by perspiration contents ions acts as a conductivity media. During ambulation the sweat rate increases as well as the temperature around feet. It indirectly increases the risk of the foot skin infection. Index of sweat ion concentration increased steeply with sweat rate. During ambulation the defensive capacity of galvanic element generated by the metallic pair will be increased. It is known, the combination of magnetic field and the different metallic coating may have synergic antimicrobial effect possible that magnetic field reduced growth of bacteria due to a paramagnetic phenomenon.

The Most Common Variant Using the Embodiment

Figure 2B:
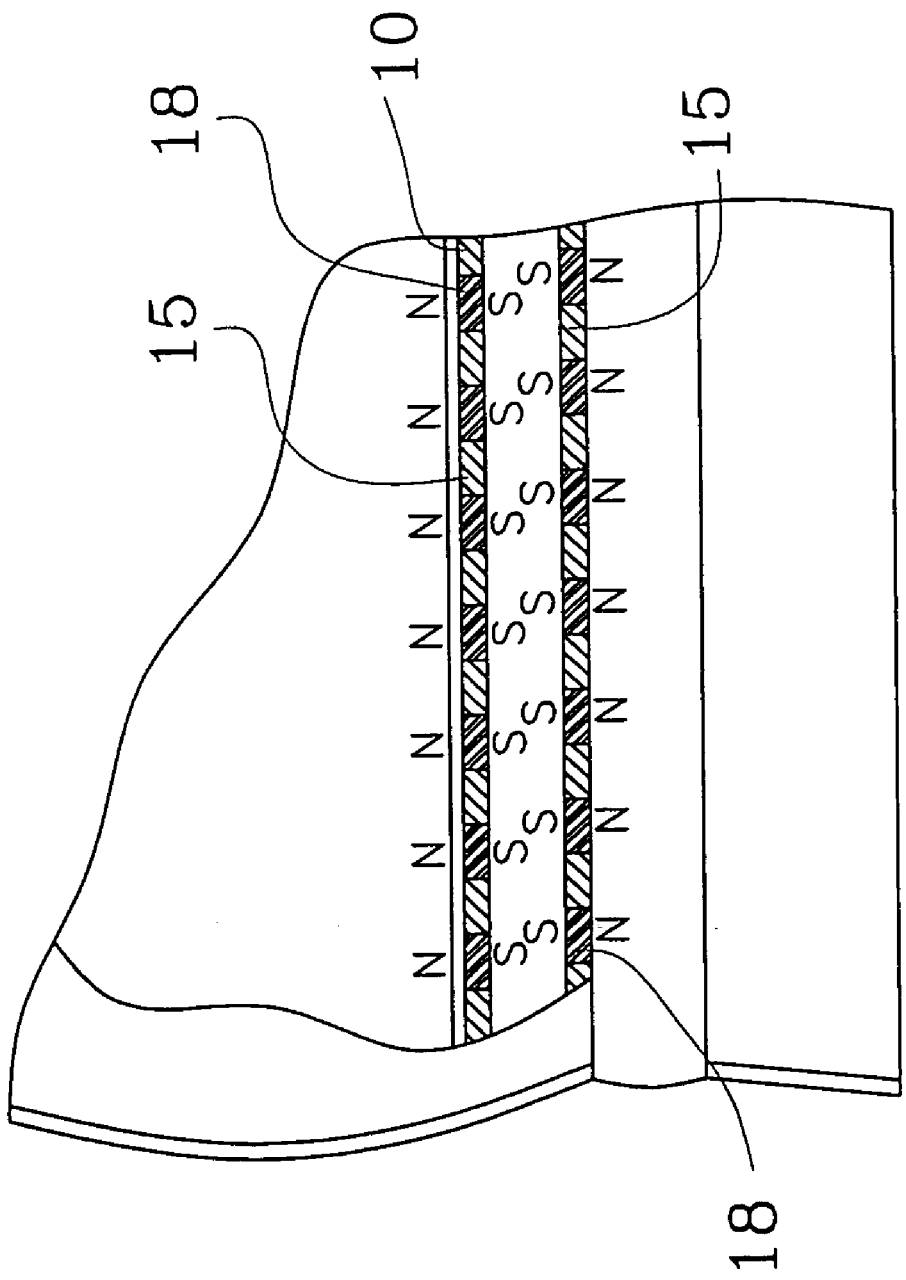
FIG. 2B represents a partial fragmentary view of the simplest variant of the embodiment for feet within a shoe.

The insole made according to the FIG. 1 or FIG. 2. During loading stages of gait a body pressure applied to the top of the cover 11. The magnetic laminas 15 move closed to each other against the force generated between two like magnetic poles. It provides shock absorbing without coils, pads and similar tools. During unloading stages of gait laminas 15 move in opposite directions provided a good energy return. The energy return happened without coils or special materials or any other similar tool. Better energy return can be explained by absence energy wasting for reshaping coils, special materials etc. The insole 10 is much more durable than known analogs with practically excluded the wear and tear of its energy return tool. During loading stages air trapped between pockets 12 and 13 moves out through perforation 16 and in the time of unloading the air will move back. It provides additional hygienic benefits of the insole 10 because of better aeration and air exchange around foot. In some cases for example at home possible to apply the insole 10 to bare feet. Client can benefit from more intense magnetic field as well as from antimicrobial property of magnetic coating.

Another application of the present invention is a possibility of exercise for different parts of body. Magnetic field provides a valuable feedback for exercise without deterioration of the device. Increasing or decreasing intensity of magnetic field can change intensity of resistance. This exercise tool can be especially useful for patients after peripheral nerve damage, stroke, contractures, and spinal cord injury. The device provides synergic effect of magnetotherapy with the heating or cooling modalities to increase effectiveness of exercise.

Examples of Body Exercise Using the Proposed Invention (The Bellow Examples of Body Exercise Given Here for the Illustration Purposes Only and Do Not Represent All Possible Applications of the Embodiment)

A. Examples of Foot Exercise:
1. In sitting or standing position put pressure downward on anterior part of foot against resistance generated by magnetic field, hold 5 sec, and than slowly release pressure. Repeat 10-15 times.
2. In sitting or standing position put pressure downward on heel against resistance generated by magnetic field, hold 5 sec, and than slowly release pressure. Repeat 10-15 times.
3. In sitting or standing position put pressure downward on lateral part of foot against resistance generated by magnetic field hold 5 sec, and than slowly release pressure. Repeat 10-15 times.
4. In sitting or standing position put pressure downward on medial part of foot against resistance generated by magnetic field, hold 5 sec, and than slowly release pressure. Repeat 10-15 times.

B. Examples of Finger Exercise:
1. Finger Adduction Exercise
   Placed rings on the second, third, fourth, and fifth fingers and a cap on the thumb as shown on FIG. 10, facing all magnets like poles to each other. Adduct all fingers against resistance generated by magnetic field hold 5 sec, and than slowly release pressure. Repeat 10-15 times.
2. Finger Abduction Exercise
   Placed rings on the third and fifth fingers and a cap on the thumb as shown on FIG. 10, facing magnets outward by South poles. Invert rings on the second and fourth fingers facing magnets outward by North poles. Abduct all fingers against resistance generated by magnetic field hold 5 sec, and than slowly release pressure. Repeat 10-15 times.

Examples of Clinical Applications the Embodiment (The Bellow Examples Clinical Applications the Embodiment Given Here for the Illustration Purposes Only and Do Not Represent All Possible Applications of the Embodiment)

1. Foot Drop
   A conventional treatment of the condition was usually relegated to bracing a limb with a device such as an ankle foot orthosis (AFO) or another type of limb brace. Such braces are bulky, uncomfortable to wear, can't be fit in any type of footwear, expensive and mostly custom-made. Part of energy return wasting for reshaping the brace itself during the gait cycle.

As shown on FIG. 4 the top lamina 15 facing like pole to the bottom anterior lamina 22 (South to South) and the bottom posterior lamina 23 faced the upper one by the opposite pole: North to South. It provides assist for foot drop.

To increase or decrease the foot drop assistance used the magnets that generate stronger or weaker magnetic field.
2. Heel Pain
   Heel pain is a very common problem in podiatric medicine.
   A conventional heel pads usually can't provide adequate protection especially in advance cases, do not provide benefits of magnetotherapy, and do not provide energy return after the heel strike stage of gait.

The proposed insole with variants of orientation of laminas 15, as shown on FIG. 5 absorbs pressure on heel, returns energy after the heel strike, as well as relieves heel pain.

As per the FIG. 5, the top lamina 15 facing by opposite pole (South to North) to the anterior bottom lamina 22 and the posterior lamina 23 faced the upper one by like pole (South to South) To increase or decrease a shock absorbing used the magnets that generate stronger or weaker magnetic field 3. Leg Length Discrepancy Conventional medicine uses other internal heel lift or external shoe platform lift depends on the severity discrepancy. The conventional lift can't be alterated, or easily changing height, change intensity shock absorbing, as well as get benefits of energy return. In addition, the conventional lifts have no benefits of magnetic field.

With the present insole physicians or client literary in seconds will be able to change height of the heel lifting or height of entire leg lift on the affected limb.

There are several possibilities using the insole to correct the leg length discrepancy:

1. "A heel lift" on the shorter leg. This construction can be used in relatively light cases of the leg length discrepancy. In this case insole 10 used only for a shorter leg. Orientation of the laminas showed on the FIG. 5. For contralateral leg used a conventional insole.
2. "A sole lift" on the shorter leg. This construction can be used in more severe cases of the leg length discrepancy: insole 10 on a shorter leg used according to FIG. 1 or FIG. 2. For contralateral leg used a conventional insole.

4. Fingers Flexion Contracture.

Insert magnetic finger caps 91, on all fingers including thumb as shown on FIG. 9. Place bar 96 across the palm. Attached bar 95 by the wrist strap 97 and place the bar 95 on the lateral aspect of the thumb contacting North poles of the bar 95 with South poles of the cap 91 placed on the thumb.

Orientation of the laminas showed on the FIG. 9.

1. Prevention and Treatment of Flexion/Extension Contracture of Upper or Lower Extremities Use two or more laminas 64 with embedded coated magnets shown on FIG. 7. The laminas 64 placed on distal and proximal parts flexion surfaces (for flexion contracture) or on extension surfaces (for extension contracture) near the affected joint. Magnets embedded in the laminas attached to the proximal part of the joint faced to like poles to the magnets embedded to the laminas attached to the distal part. If the affected part of the body dressed, said laminas can be attached to the dressing materials by Velcro®, or similar means. The laminas 64 made from stretchable polymer materials provided the proposed device additional therapeutic benefits by possibility of heating or cooling therapy.

6. Unload the Affected Extremity

Use two or more laminas with embedded magnet as shown on FIG. 7 or solid magnets. The laminas made from stretchable polymer materials provided the proposed device with possibility of heating or cooling therapy. One set of the laminas or solid magnets placed on affected part of extremity and another set of said laminas or solid magnets placed on bed parallel to the first one. Magnets embedded in the laminas or solid magnets attached to the affected part of the extremity faced to like poles to the magnets embedded to said laminas or solid magnets attached to the bed.

If the affected part of the body dressed, said laminas can be attached to the dressing materials by Velcro® or similar means.

Special Circumstancing of Using the Present Invention

1. In some instance the intense magnetic filed is not desirable. Patients with pacemakers and pregnant women are most common examples. With minimizing intensity of the magnetic field and preserved all other benefits of the proposed insole such as shock absorbing and energy return some modifications of the proposed insole can be safety used.

In such cases in the top pocket 12 above lamina 15 (see FIG. 1) inserted the magnetic shield 17 made from the thin foil with thickness 0.002-0.095 inches. Examples of such foil may be the EMF foil that contains an 80% nickel alloy. The EMF foil widely used in an industry to shield delicate electronic components as well as for the home and office use.

2. Some patients need to relive foot pain prior of ambulation. Applications of heating or cooling modalities to soles can be a simple solution. One of examples of such situation is plantar fasciitis when the most severe pain patients experience during the first steps after prolonging resting. In such cases the embodiment represented on FIG. 2 would be particular helpful.

The present device can provide synergic effect of magnetotherapy with the heating or cooling modalities application.

In this case the device placed in a microwave oven for 3-5 min for heating therapy or refrigerator—for cool therapy, also for 3-5 minutes.

Using the Proposed Invention During the Space Missions (The Bellow Examples of Using the Proposed Invention During the Space Missions Given Here for the Illustration Purposes Only and Do Not Represent All Possible Applications of the Embodiment)

Weightless and absence of natural Earth magnetic field listed among causes of changing of functional status of organisms especially during prolonging Space During the space missions weightless environment causes muscle atrophy including feet muscle atrophy resulting in flat feet with collapse of medial and lateral arches.

The special variants of the insole of present invention can be helpful to partially minimized side effects of the above problems For imitation of the Earth magnetic field used several special variants of the proposed insole. Variants of the insole 10 for the Space mission presented on FIGS. 6 and 8. Magnetic sock 60 (FIG. 6) represents modified top magnetic lamina 15 presented on FIG. 1 and magnetic base 61 is a modified bottom magnetic lamina 15.

The sock 60 has two portions: a lower (plantar) portion 62 and an upper (dorsal) upper side 63.

The lower portion 62 has a "galosh-like" shape. The lower portion 62 and the upper portion 66 of magnetic base 61 should follow the contour of the medial and lateral arches of astronaut's foot before the Space mission. The sock 60 preferably should be a custom-made. Such construction of said magnetic sock helps to preserve a prior of mission anatomy including the arches preservation.

The lower portion 62 is a mesh "galosh" made from magnetic laminas 64 embedded in nonmagnetic materials. The nonmagnetic materials made from fibers 65. Examples of such fibers are cotton and/or synthetic fibers in conjunction with silver and gold fibers. Upper portion 63 made from nonmagnetic fibers 65. The upper side 66 of the magnetic base 61 faced to lower portion 62 of the magnetic sock 60 and contralateral side 67 of the lamina 61 attached to the magnetic shield layer 68. The magnetic shield 68 has an adhesive layer 69 attached to the inner side of boot.

The magnetic laminas 64 (see FIG. 7) have dual advantages: they act as a source of magnetic field and have antimicrobial properties because of the silver-gold platting.

The outer and inner parts of the magnetic laminas 64 have uniform polarity: for example South Pole on an outer part and North Pole on an inner one or vise versa. However, the North Pole on an inner side of the sock variant is preferable. The upper side 66 of the magnetic base 61 and the lower portion 62 of the magnetic sock 60 has uniform polarity. The sides 62 and 66 can have either same or different polarity. The magnetic shield layer 68 can arm a contra lateral side 67. The magnetic shield 68 made from foil or other magnetic-shielding materials, for example Giron® magnetic shielding film or the already mention EMF foil. The magnetic shield 68 has an adhesive layer 69 (for example Velcro) that can attach to the inner side of boot. The magnetic shielding keeps the magnetic field inside the boot from interfering with equipments outside of the boot.

Magnetic sock 60 with or without the magnetic base 61 can be used for patients with the circulatory problems and foot skin infection. Patient will have advantages of synergetic antibacterial and antifungal properties of above-mentioned dual metallic application and magnetic field. In such case application of South Pole to skin is preferable.

The design of the sock 60 provides not only adequate magnetic environment for feet but also helps to eliminate common bacteria, fungi, and odors and doesn't interfere with perspiration. To better control for the magnetic environment of legs instead the magnetic sock 60 may be used the magnetic half-hose 80. (FIGS. 8A and 8B) Similar to the magnetic sock 60, the magnetic half-hose 80 made from the mesh containing the magnetic laminas 64 embedded in a nonmagnetic base. The base made from nonmagnetic fibers 65. Examples of such fibers are cotton and/or synthetic fibers in conjunction with silver and gold fibers. (Fibers 64 and 65 don't show on FIG. 8). The half hose surrounded by magnetic lamina 81 armed by magnetic shield 82 and attached to the inner side of the astronaut's boot 83. The magnetic shield 82 made from thin foil or other magnetic-shielding materials, for example Giron® magnetic shielding film or the already mention EMF foil.

Important benefit of the proposed magnetic sock 60 and magnetic half hose 80 is the possibility of using them as an exercise tool.

Examples of Exercise Using Said Magnetic Sock and Magnetic Half Hose (The Bellow Examples of Exercise Using said Magnetic Sock and Magnetic Half Hose Given Here for the Illustration Purposes Only and Do Not Represent All Possible Applications of the Embodiment)

A. Magnetic sock 60 and magnetic base 61 or magnetic half hose 80 and magnetic base 61 or magnetic lamina 81 faced to each other by like poles: North to North or South to South (FIG. 8A for magnetic half hose)

Figure 8B:
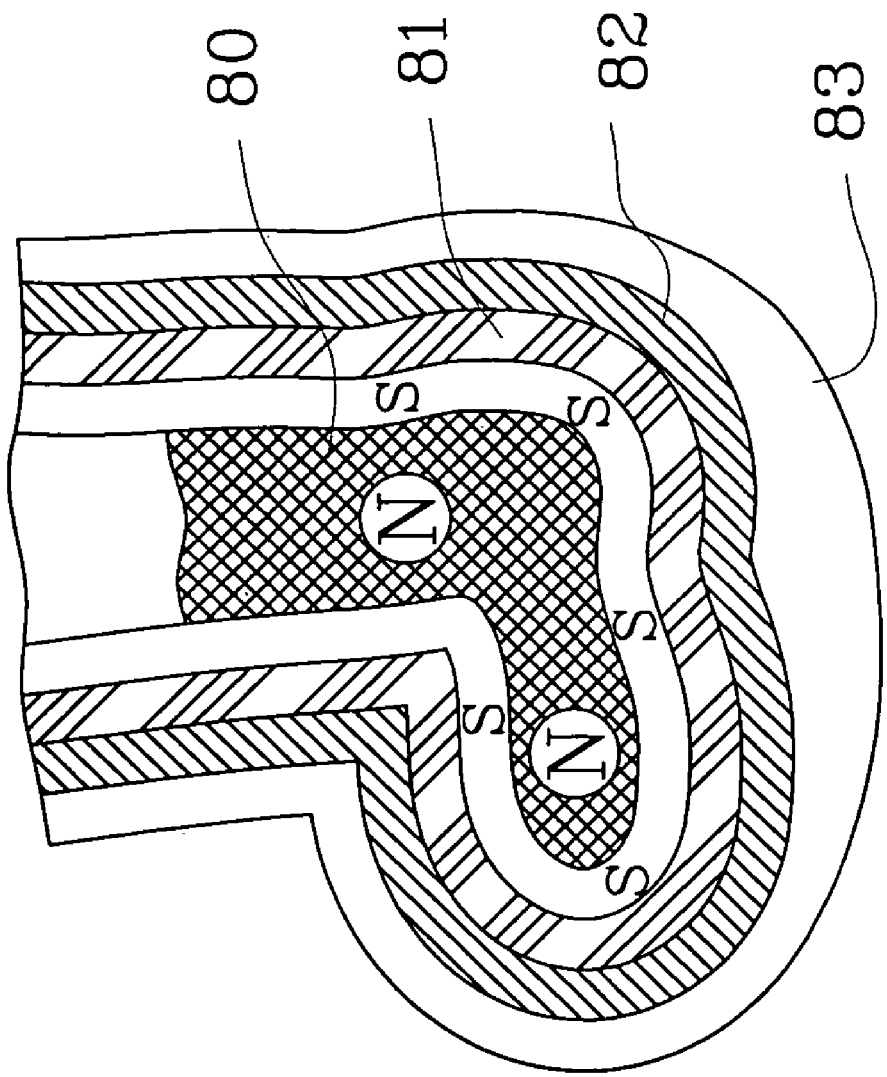

1. Move feet toes direct to magnetic base 61 or magnetic lamina 81 against resistant generated by magnetic field, hold 5 sec, and slowly return to the initial position. Repeat 10-15 times 2. Move heels direct to magnetic base 61 or magnetic lamina 81 against resistant generated by magnetic field, hold 5 sec, and slowly return to the initial position. Repeat 10-15 times 3. Move lateral parts of feet direct to magnetic base 61 or magnetic lamina 81 against resistant generated by magnetic field, holds 5 sec, and slowly returns to the initial position. Repeat 10-15 times 4. Move medial parts of feet direct to magnetic base 61 or magnetic lamina 81 against resistant generated by magnetic field, holds 5 sec, and slowly returns to the initial position. Repeat 10-15 times B. Magnetic base 61 or magnetic lamina 81 faced to each other by opposite poles: North to South or South to North (FIG. 8B for magnetic half hose)

1. Move feet toes in direction opposite to magnetic base 61 or magnetic lamina 81 against resistant generated by magnetic field, hold 5 sec, and slowly return to the initial position. Repeat 10-15 times 2. Move heels in direction opposite to magnetic base 61 or magnetic lamina 81 against resistant generated by magnetic field, hold 5 sec, and slowly return to the initial position. Repeat 10-15 times 3. Move lateral parts of feet in direction opposite to magnetic base 61 or magnetic lamina 81 against resistant generated by magnetic field, hold 5 sec, and slowly return to the initial position. Repeat 10-15 times 4. Move medial parts of feet in direction opposite to magnetic base 61 or magnetic lamina 81 against resistant generated by magnetic field, hold 5 sec, and slowly return to the initial position. Repeat 10-15 times.

What is claimed is:

1. A medical and recreational device comprising:
   A sock and an astronaut's boot;
      wherein the sock comprises:
         at least two laminas, wherein each of the at least two laminas have magnetic field sources;
         wherein the magnetic field sources located on a first lamina of the at least two laminas face the magnetic field sources on the second lamina of the at least two laminas; and wherein at least one lamina of the at least two laminas is configured to be attached to a treated body part;
         wherein the sock is made from non-magnetic materials embedded with said laminas;
      and the astronaut's boot comprises;
         A magnetic shield; and
         a magnetic base;
            wherein the magnetic shield surrounds the inner side of the astronaut's boot and is affixed to the astronaut's boot by an adhesive layer;
            wherein the magnetic base comprises another magnetic field source;
            wherein a bottom of the magnetic base is attached to the magnetic shield;
         wherein the sock is configured to be worn on a foot and the sock is placed within the astronaut's boot above the magnetic base such that the magnetic field sources of the bottom lamina of the of the first and second lamina of the at least two laminas and the magnetic base face each other.
   wherein each of the at least two laminas are comprised of one top and one bottom lamina;
   wherein the magnetic field sources of each of the at least two laminas has at least one magnetic field source surrounded by non-magnetic materials;
   wherein the magnetic field sources are constant magnets;
   wherein the magnets have metallic coatings made from different metals with antimicrobial properties;
   wherein the non-magnetic materials are made with a stretchable polymer to provide shock absorbing and energy returning properties.

2. The medical and recreational device of claim 1 wherein the magnetic field sources are constant magnets.

3. The medical and recreational device of claim 1 wherein the magnetic field sources are electromagnets.

4. The medical and recreational device of claim 1 wherein all magnetic field sources are configured to be placed above a treated body part.

5. The medical and recreational device of claim 1 wherein all magnetic field sources are configured to be placed below a treated body part.

6. The medical and recreational device of claim 1 wherein at least one of the magnetic field sources is configured to be placed above a treated body part and at least another magnetic field source is configured to be placed below the treated body part.

7. The medical and recreational device of claim 1, wherein said at least one of the laminas configured to surround the treated body part.

8. The medical and recreational device of claim 1
wherein each of the at least laminas are comprised of one top and one bottom lamina;
wherein the magnetic field sources of each of the at least two laminas has at least one magnetic field sources surrounded by non-magnetic materials;
wherein the magnetic field sources are constant magnets;
wherein magnets have metallic coatings made from different metals with antimicrobial properties;
wherein the non-magnetic material are made with stretchable polymer to provide shock absorbing and energy returning properties.

9. The medical and recreational device of claim 1
wherein each of the at least laminas are comprised of one top and one bottom lamina;
wherein the magnetic field sources of each of the at least two laminas has at least two magnetic field sources surrounded by non-magnetic materials;
wherein a posterior part of the bottom lamina has all magnetic field sources facing unlike poles of the magnetic sources of the top lamina;
wherein an anterior part of the bottom lamina has magnetic field sources facing like poles of the magnetic field sources of the top lamina.

10. The medical and recreational device of claim 1
wherein each of the at least two laminas are comprised of one top and one bottom lamina;
wherein the magnetic field sources of each of the at least two laminas has at least two magnetic field sources surrounded by non-magnetic materials;
wherein an anterior part of the bottom lamina has all magnetic field sources facing unlike poles of the magnetic sources of the top lamina;
wherein a posterior part of the bottom lamina has magnetic field sources facing like poles of the magnetic field sources of the top lamina.

11. The recreational device of claim 1
wherein each of the at least two laminas are comprised of one top and one bottom lamina;
wherein the magnetic field sources of each of the at least two laminas has at least two magnetic field sources surrounded by non-magnetic materials;
wherein one lamina of the at least two laminas is configured to be attached to a proximal part of a flexor surface of an affected joint and another lamina of said laminas is configured to be attached to a distal part of the flexor surface of an affected joint;
wherein each of the at least two laminas face each other so that the magnetic field sources have like poles facing each other.

* * * * *